(12) United States Patent
Charrier et al.

(10) Patent No.: US 9,018,740 B2
(45) Date of Patent: Apr. 28, 2015

(54) SENSOR WITH FIELD EFFECT TRANSISTOR HAVING THE GATE DIELECTRIC CONSISTING OF A LAYER OF LIPIDS AND METHOD OF FABRICATING THIS TRANSISTOR

(71) Applicants: Anne Charrier, Marseilles (FR); Hervé Dallaporta, Marseilles (FR); Tuyen Nguyen Duc, Marseilles (FR)

(72) Inventors: Anne Charrier, Marseilles (FR); Hervé Dallaporta, Marseilles (FR); Tuyen Nguyen Duc, Marseilles (FR)

(73) Assignee: Centre National de la Recherche Scientifique (C.N.R.S) (FR)

( * ) Notice: Subject to any disclaimer, the term of this patent is extended or adjusted under 35 U.S.C. 154(b) by 0 days.

(21) Appl. No.: 14/361,026

(22) PCT Filed: Nov. 30, 2012

(86) PCT No.: PCT/EP2012/074114
§ 371 (c)(1),
(2) Date: May 28, 2014

(87) PCT Pub. No.: WO2013/083490
PCT Pub. Date: Jun. 13, 2013

(65) Prior Publication Data
US 2014/0264473 A1   Sep. 18, 2014

(30) Foreign Application Priority Data
Dec. 6, 2011   (FR) ...................................... 11 61241

(51) Int. Cl.
*H01L 23/58*   (2006.01)
*H01L 51/40*   (2006.01)
(Continued)

(52) U.S. Cl.
CPC ........ *G01N 27/414* (2013.01); *H01L 21/28185* (2013.01); *H01L 29/51* (2013.01)

(58) Field of Classification Search
USPC ................... 257/40, 253, 642, 759, E39.007, 257/E51.007, E51.045, E21.117; 438/49, 438/82, 99, 197, 260, 623
See application file for complete search history.

(56) References Cited

U.S. PATENT DOCUMENTS

| | | | |
|---|---|---|---|
| 4,490,216 A | | 12/1984 | McConnel |
| 4,637,861 A | * | 1/1987 | Krull et al. ................ 205/782.5 |
| 5,466,348 A | * | 11/1995 | Holm-Kennedy ............ 205/775 |
| 5,491,097 A | * | 2/1996 | Ribi et al. .................... 436/518 |

(Continued)

FOREIGN PATENT DOCUMENTS

EP      2 317 306 A1    5/2011

OTHER PUBLICATIONS

International Search Report dated Feb. 5, 2013 issued in corresponding International patent application No. PCT/EP2012/074114.
(Continued)

*Primary Examiner* — Thanh V Pham
(74) *Attorney, Agent, or Firm* — Ostrolenk Faber LLP

(57) ABSTRACT

A field effect transistor (1) including: a semiconducting substrate (2) having two areas doped with electric charge carriers forming a source area (3) and a drain area (4), respectively; a dielectric layer positioned above the semiconducting substrate (2) between the source (3) and the drain (4) and forming the gate dielectric (9) of the field effect transistor (1); a gate (11) consisting of a reference electrode (8) and of a conductive solution (10), the solution (10) being in contact with the gate dielectric (9); and the gate dielectric (9) consists of a layer of lipids (13) in direct contact with the semiconducting layer (2). The invention also relates to a method for manufacturing such a field effect transistor (1) is disclosed.

11 Claims, 2 Drawing Sheets

(51) Int. Cl.
  *G01N 27/414* (2006.01)
  *H01L 21/28* (2006.01)
  *H01L 29/51* (2006.01)

(56) References Cited

U.S. PATENT DOCUMENTS

| | | | |
|---|---|---|---|
| 5,500,188 A * | 3/1996 | Hafeman et al. | 204/403.01 |
| 7,169,272 B2 * | 1/2007 | Fritsch et al. | 204/403.01 |
| 7,244,349 B2 * | 7/2007 | Vogel et al. | 205/777.5 |
| 2007/0224637 A1 * | 9/2007 | McAuliffe et al. | 435/7.1 |
| 2012/0265596 A1 * | 10/2012 | Mazed et al. | 705/14.23 |

OTHER PUBLICATIONS

Anne Charrier et al.: "Direct Stabilization of a Phospholipid Monolayer on H-Terminated Silicone", Langmuir, vol. 26, No. 4, Feb. 16, 2010, pp. 2538-2543, XP055029513.

Ottenbacher D. Et al.: "Developing biosensors with pH-ISFET transducers utilizing lipid bilayer membranes with transport proteins", Sensors and Actuators B: Chemical: International Journal Devoted to Research and Development of Physical and Chemical Transducers, Elsevier S.A., Switzerland, vol. 6, No. 1-3, Jan. 1, 1992, pp. 192-196, XP026553219.

* cited by examiner

SENSOR WITH FIELD EFFECT TRANSISTOR HAVING THE GATE DIELECTRIC CONSISTING OF A LAYER OF LIPIDS AND METHOD OF FABRICATING THIS TRANSISTOR

CROSS REFERENCE TO RELATED APPLICATIONS

The present application is a 35 U.S.C. §371 National Phase conversion of PCT/EP2012/074114, filed Nov. 30, 2012, which claims benefit of French Application No. 11 61241, filed Dec. 6, 2011, the disclosure of which is incorporated herein by reference. The PCT International Application was published in the French language.

TECHNICAL FIELD OF THE INVENTION

The present invention relates to a field effect transistor which may notably be used as a sensor.

BACKGROUND OF THE INVENTION

More specifically, the invention relates to a field effect transistor including:
- a semiconducting substrate having two areas doped with electric charge carriers respectively forming a source area and a drain area;
- a dielectric layer positioned above the semiconducting substrate between the source and the drain and forming the dielectric gate of the field effect transistor; and
- a gate consisting of a reference electrode and of a conducting solution, the conducting solution being in contact with the gate dielectric.

The invention also relates to a method for manufacturing such a field effect transistor.

Field effect transistors of this type are already known in the state of the art.

When a change in charges occurs at the surface of the gate dielectric, for example, when charged molecules or ions are positioned at the surface of the gate dielectric or by applying a gate voltage, the electric charge carriers present in the source and the drain are attracted into the semiconducting substrate under the gate dielectric by an electric field and may form a so-called conduction channel. A current then flows between the source and the drain. The transistor is then in a so-called conductive state. The width of the conduction channel and the intensity of the current which flows between the source and the drain depend on the charge present at the surface of the gate dielectric.

The most commonly encountered transistors in the state of the art have a gate dielectric formed with an inorganic material such as silicon dioxide ($SiO_2$).

This type of transistor, although having interesting electric properties is not optimal for detecting charged biological molecules or ions in solution. On the other hand, the method for manufacturing this type of transistor comprises a step for thermal oxidation of silicon, which is often lengthy and which requires annealing in a temperature range which may extend up to 800° C.

In the state of the art, field effect transistors are also encountered which include a gate dielectric formed with an organic material. The main drawback of this type of transistor lies in the fact that the organic material layer forming the gate dielectric has a large thickness, which reduces the electric performances of the transistor. Indeed, the larger the thickness of the gate dielectric, the more the voltage to be applied to the gate for forming the conduction channel has to be high.

This type of transistor is therefore not optimal for detecting or studying biological molecules which do not support high voltages.

SUMMARY OF THE INVENTION

The object of the invention is to provide a field effect transistor which may be used as a sensor, and having a gate dielectric with high sensitivity for low voltages imposed to the gate.

The object of the invention is also to provide a method for manufacturing such a field effect transistor.

For this purpose, the invention relates to a field effect transistor including:
- a semiconducting substrate having two areas doped with electric charge carriers respectively forming a source area and a drain area;
- a dielectric layer positioned above the semiconducting substrate between the source and the drain and forming the gate dielectric of the field effect transistor;
- a gate consisting of a reference electrode and of a conductive solution, the conductive solution being in contact with the gate dielectric;

characterized in that the gate dielectric consists of a layer of lipids in direct contact with the semiconducting substrate.

According to other features of the invention taken alone or as a combination:
- the layout of lipids is a single layer or a bi-layer of lipids;
- the layer of lipids has a thickness comprised between 2 and 8 nm and preferably comprised between 2.4 and 3 nm.
- the layer of lipids comprises synthetic lipids;
- the layer of lipids is stable in an air medium and in a liquid medium; and
- the semiconducting substrate includes a lower face in contact with an insulating material layer, the insulating material layer being itself in contact with a rear gate consisting of a conductive material.

According to a second aspect, the invention deals with a method for manufacturing a field effect transistor according to any of the preceding claims, comprising:
- a step for forming doped areas forming the source and the drain;
- a step for making the gate dielectric;

characterized in that the step for making the gate dielectric comprises a step for forming the layer of lipids on the semiconducting substrate by condensation and merging of vesicles on the semiconducting substrate.

According to other features of this aspect of the invention taken alone or as a combination:
- the step for making the gate dielectric comprises a step for cooling the semiconducting substrate;
- the step for making the gate dielectric comprises a step for rinsing the layer of lipids; and
- the step for making the gate dielectric comprises a step for stabilizing the layer of lipids by two-dimensional polymerization.

BRIEF DESCRIPTION OF THE DRAWINGS

The invention will be better understood by means of the description which follows, only given as an example and made with reference to the appended drawings, wherein.

DESCRIPTION OF PREFERRED EMBODIMENTS

Figure 1:
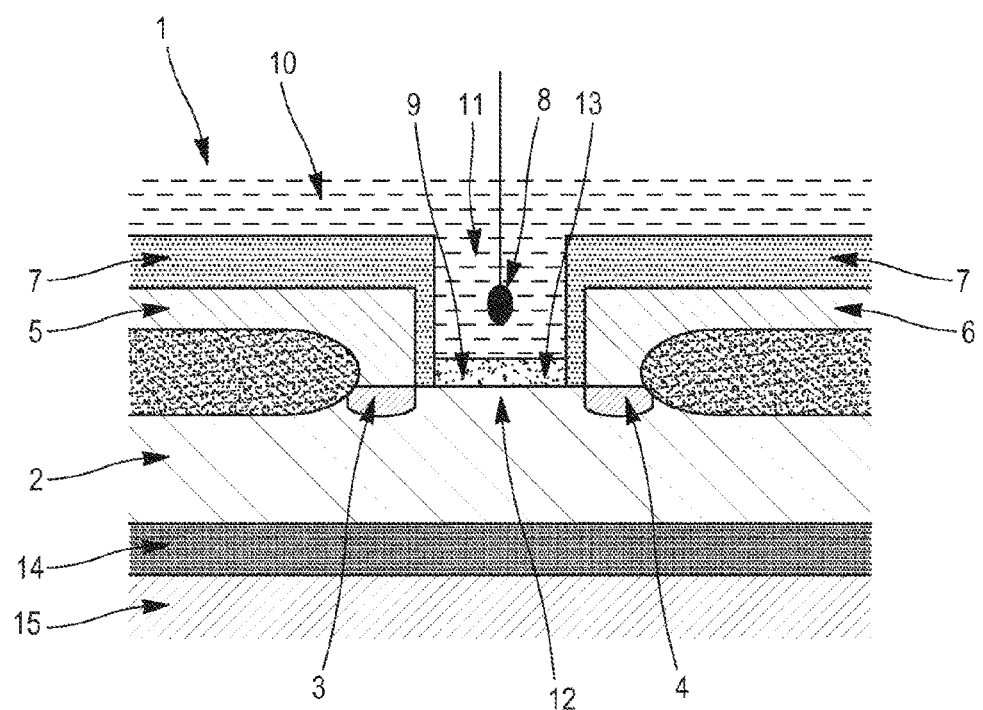
FIG. 1 illustrates a sectional view of a field effect transistor according to the invention.

Indeed, a field effect transistor designated by the general reference 1 is illustrated in FIG. 1.

Conventionally and as this has been described above, this transistor 1 comprises a semiconducting substrate 2.

The semiconducting substrate 2 is preferably formed with an inorganic material, such as silicon, graphite or further germanium. The use of an inorganic material such as silicon has the advantage of being able to be produced on a large scale and with a low cost.

The semiconducting substrate 2 may alternatively be formed with an organic material such as a conductive polymer, for example PEDOT:PSS. PEDOT:PSS is a mixture of two polymers, poly(3,4-ethylenedioxythiophene) (PEDOT) and sodium poly(styrene sulfonate) (PSS).

The transistor 1 further has two strongly doped areas with electric charge carriers designated by the general references 3 and 4. These areas 3 and 4 make up the source and the drain respectively.

Conventionally, the source 3 and the drain 4 are covered with a conductive material layer playing the role of an electric contact.

In FIG. 1, the electric contacts are designated by the general references 5 and 6.

The electric contacts 5 and 6 for example are made in aluminum.

The electric contacts 5 and 6 are conventionally covered with an insulating layer.

In FIG. 1, this insulating layer is designated by the general reference 7.

The insulating layer 7 for example consists of silicon nitride (SiN) or of a polymer such as SU-8.

The transistor 1 also has a reference electrode, designated by the general reference 8 in FIG. 1.

Also conventionally, the transistor 1 has a dielectric layer positioned above the semiconducting substrate 2 between the source 3 and the drain 4 and forming the gate dielectric, or designated by the general reference 9, of the field effect transistor 1.

The transistor 1 also comprises a conductive solution, designated by the general reference 10, located above the gate dielectric 9.

The conductive solution 10 is in contact with the gate dielectric 9.

The conductive solution 10 and the reference electrode 8 formed the gate, designated by the general reference 11, of the field effect transistor 1.

Thus, the insulating layer 7 allows insulation of the electric contacts 5 and 6 of the conductive solution 10.

When a change in the charges occurs at the surface of the gate dielectric 9, for example when charged molecules or ions are positioned that the surface of the gate dielectric 9 or by application of a gate voltage, the electric charge carriers present in the source 3 and the drain 4 are attracted in the semiconducting substrate 2 and of the gate dielectric 9 by an electric field and may form a so-called conduction channel. This conduction channel is designated by the general reference 12 in FIG. 1. A current then flows between the source 3 and the drain 4. The width of the conduction channel 12 and therefore the intensity of the current depend on the charge present at the surface of the gate dielectric 9.

The gate dielectric 9 according to the invention consists of a layer of lipids in a designated by the general reference 13.

This layer of lipids 13 has the advantage of having good electric characteristics, such as a low leakage current, a breakdown voltage of the order of 10 MV/cm, as well as a low density of interface defects. The interface defects are generally charges or voids trapped at the interface between the semiconducting substrate 2 and the gate dielectric 9 and/or inside the gate dielectric 9. These interface defects tend to cancel out a portion of the charges present at the surface of the gate dielectric 9 and therefore tend to reduce the sensitivity of the field effect transistor 1. In the field effect transistor 1 according to the invention, the layer of lipids 13 has a density of interface defects of the order of $5.10^9/cm^2$. This low value of the interface defect density represents a clear improvement as compared with the inorganic and gate dielectrics for example consisting of silicon oxide ($SiO_2$), zirconium oxide ($ZrO_2$), hafnium oxide ($HfO_2$), or yttrium oxide ($Y_2O_3$), which have an interface defect density substantially equal to $10^{11}/cm^2$.

Thus, with this layer of lipids 13, the transistor may exhibit high electric performances and adapted to the detection of any charged object, such as charged molecules or ions.

According to the invention, this layer of lipids 13 is in direct contact with the semiconducting substrate 2.

Advantageously, the layer of lipids 13 is a single layer or a bilayer of lipids.

Advantageously, the layer of lipids 13 has a thickness comprised between 2 and 8 nm, and preferably comprised between 2.4 and 3 nm. This thickness for example has the value of 2.7 nm.

Thus, with this layer of lipids 13, the transistor 1 may have high sensitivity when low voltages are imposed to the gate 11. For example, this is the case when charged molecules or ions are positioned at the surface of the gate dielectric 9. In this example, the voltages imposed to the gate are typically less than 2 V.

Also advantageously, the layer of lipids 13 comprises synthetic lipids. These synthetic lipids are for example low-cost synthetic lipids. For example, 1,2-bis(10,12-tricosadiynoyl)-sn-glycero-3-phosphocholine may be used for making the layer of lipids 13.

Further, the layer of lipids 13 is advantageously stable in an air medium and in a liquid medium.

Moreover, the semiconducting substrate 2 advantageously includes a lower face in contact with an insulating material layer, itself in contact with a rear gate consisting of a conductive material.

In FIG. 1, the insulating material layer is designated by the general reference 14 and the rear gate is designated by the general reference 15.

The rear gate 15 when a voltage is applied to it, gives the possibility of modifying the width of the conduction channel 12 and of optimizing the detection conditions. It thus allows an increase in the sensitivity of the field effect transistor 1.

The insulating material layer 14 for example consists of silicon dioxide ($SiO_2$) or of an insulating polymer.

The rear gate 15 for example consists of silicon and/or of a conductive polymer.

Figure 2:
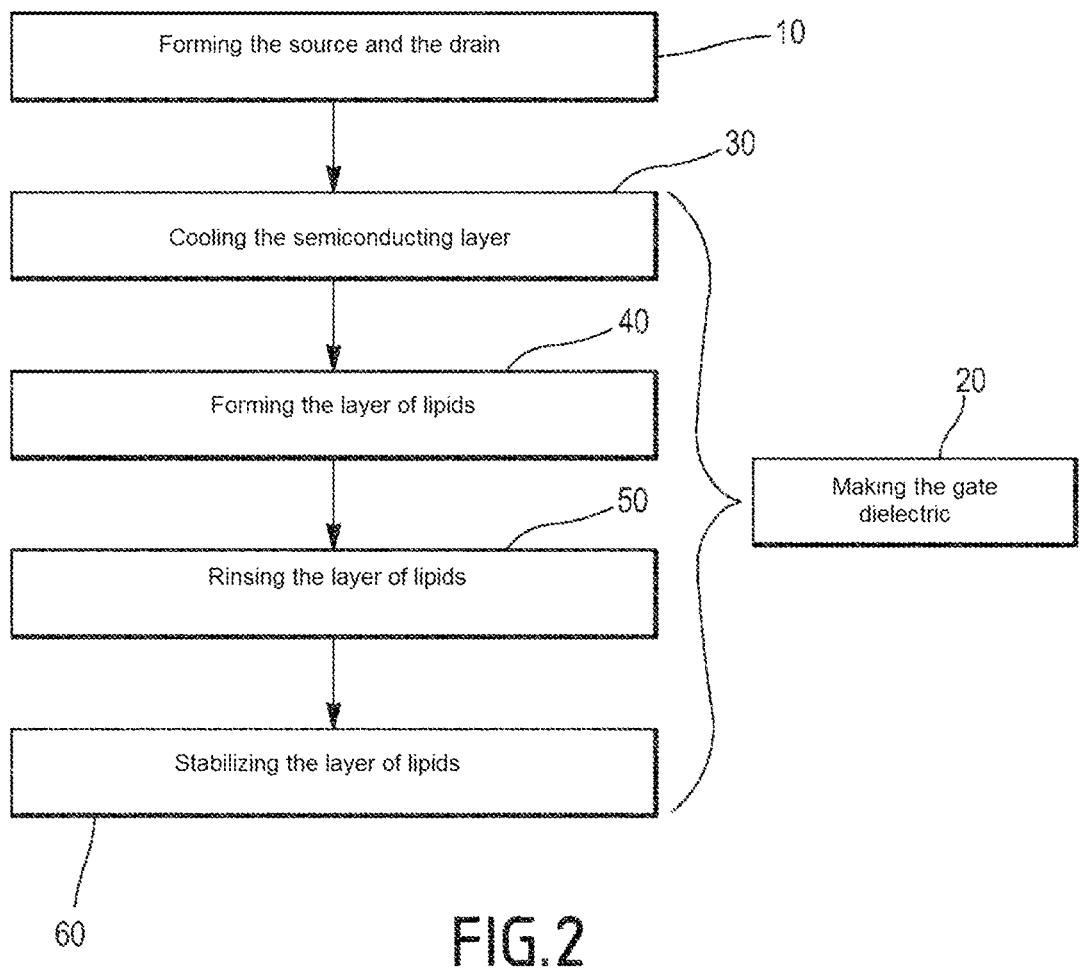
FIG. 2 illustrates a flow chart of the operation of the method for manufacturing a field effect transistor according to the invention.

An embodiment of the method for manufacturing the transistor 1 according to the invention will now be described by means of FIG. 2.

Conventionally, the manufacturing method begins in step 10 by forming the areas making up the source 3 and the drain 4.

Conventionally, the formation of these areas 3 and 4 comprises a step for doping with the n (or p) charge carriers.

Strongly doped source 3 and drain 4 are thereby obtained relatively to the semiconducting substrate 2.

The method according to the invention conventionally continues with a step for making electric contacts 5 and 6 on the source 3 and the drain 4.

The method continues, also conventionally, with a step for isolating electric contacts 5 and 6, for example by depositing the insulating layer 7. The method then comprises a step 20 for making the gate dielectric 9.

This step advantageously comprises a first step 30 cooling the semiconducting substrate 2. The semiconducting substrate 2 is for example called to a temperature substantially equal to 10° C.

The layer of lipids 13 is then formed in step 40 by condensation of lipid vesicles causing merging of said lipid vesicles on the semiconducting substrate 2.

With the step 30 for cooling the semiconducting substrate 2, it is possible to initiate the step 40 for forming the layer of lipids 13, by condensing the lipid vesicles.

The step 20 for making the gate dielectric 9 advantageously continues with the step 50 for rinsing the layer of lipids 13. With this step, it is possible to remove possible overlayers of lipids which are less stable than the layer of lipids 13 in direct contact with the semiconducting substrate 2.

The step 20 for making the gate dielectric 9 ends with a step 60 stabilizing the layer of lipids 13 by two-dimensional polymerization.

This step 60 requires a temperature range comprised for example between 10° and 45° C.

It is thus understood that the field effect transistor according to the invention has characteristics allowing it to form a detector with good sensitivity by using low gate voltages.

The method for making the gate dielectric described above thus gives the possibility of obtaining an ultra-thin homogeneous gate dielectric stable in air and in a liquid medium. A field effect transistor particularly adapted for detecting and studying charged biological molecules or ions in solution is thereby obtained.

Moreover, the use of a layer of lipids as a gate dielectric gives the possibility of avoiding the conventional step for thermal oxidation of the silicon which is often long and which requires annealing in a temperature range which may extend up to 800° C. This low temperature manufacturing method is further compatible with the steps for manufacturing microelectronic devices.

The terms of <<semiconducting layer>> and of <<semiconducting substrate>> are equivalent here and are both equally used.

The step for cooling the semiconducting layer firstly allows the merging of the lipid vesicles at the surface of the semiconducting layer.

Secondly, the step for cooling the semiconducting layer gives the possibility of facilitating polymerization of the layer of lipids. Indeed, cooling the semiconducting layer causes a reduction in the space occupied by the lipids, and therefore densification of the layer of lipids. As the mobility of lipids in a dense layer of lipids is reduced, polymerization of the layer of lipids required for its stability in air will be facilitated.

What is claimed is:

1. A field effect transistor including:
    a semiconducting substrate having two areas doped with electric charge carriers forming a source area and a drain area, respectively;
    a dielectric layer positioned above the semiconducting substrate between the source and the drain and forming the gate dielectric of the field effect transistor;
    a gate consisting of a reference electrode and of a conductive solution, the conductive solution being in contact with the gate dielectric;
    wherein the gate dielectric consists of a layer of lipids in direct contact with the semiconducting substrate.

2. The field effect transistor according to claim 1, wherein the layer of lipids is a single layer or a bilayer of lipids.

3. The field effect transistor according to claim 1, wherein the layer of lipids has a thickness comprised between 2 and 8 nm.

4. The field effect transistor according to claim 3, wherein the layer of lipids has a thickness comprised between 2.4 and 3 nm.

5. The field effect transistor according to claim 1, wherein the layer of lipids comprises synthetic lipids.

6. The field effect transistor according to claim 1, wherein the layer of lipids is stable in an air medium and in a liquid medium.

7. The field effect transistor according to claim 1, wherein the semiconducting substrate includes a lower face in contact with an insulating material layer, the insulating material layer being itself in contact with a rear gate consisting of a conductive material.

8. A method for manufacturing a field effect transistor according to claim 1, comprising:
    a step for forming doped areas making up the source and the drain;
    a step for making the gate dielectric;
    wherein the step for making the gate dielectric comprises a step for forming the layer of lipids on the semiconducting substrate by condensation and merging of lipid vesicles on the semiconducting substrate.

9. The method according to claim 8, wherein the step for making the gate dielectric comprises a step for cooling the semiconducting layer.

10. The method according to claim 8, wherein the step for making the gate dielectric comprises a step for rinsing the layer of lipids.

11. The method according to claim 8, wherein the step for making the gate dielectric comprises a step for stabilizing the layer of lipids by two-dimensional polymerization.

* * * * *